United States Patent [19]

Roberts

[11] Patent Number: 5,183,757
[45] Date of Patent: Feb. 2, 1993

[54] PROCESS FOR THE PRODUCTION, DESICCATION AND GERMINATION OF CONIFER SOMATIC EMBRYOS

[75] Inventor: Dane R. Roberts, Vancouver, Canada

[73] Assignee: British Columbia Research Corporation, Vancouver, Canada

[21] Appl. No.: 388,598

[22] Filed: Aug. 1, 1989

[51] Int. Cl.$^5$ ............................ C12N 5/00; A01C 1/06
[52] U.S. Cl. ........................... 435/240.49; 435/240.45; 435/240.54; 47/57.6; 47/DIG. 9
[58] Field of Search ...................... 435/240.45, 240.48, 435/240.49, 240.54; 47/DIG. 9, 47-56, 58

[56] References Cited

FOREIGN PATENT DOCUMENTS 8905575 6/1989 World Int. Prop. O. .

OTHER PUBLICATIONS

Hakman et al. 1988, Physiol. Plant. 72(3): 579–587.
Becwar et al. 1987, TAPPI J 70(4): 155–160.
Hammatt et al. 1987. J. Plant Physiol. 128(3): 219–226.
Boulay et al. 1988. Plant Cell Reports 7: 134–137.
Bewley, J. D. and Black, M. (1985) "Maturation Drying, The Effects of Water Loss on Development in Seeds"; Physiology of Plant Development, Chapter 2.4; Plenum Press N.Y.; pp. 70–73.
Becwar, M. R. et al; "Maturation, Germination, and Conversion of Norway Spruce Somatic Embryos to Plants" (1989), In Vitro Cell. & Dev. Biol. 25: 575–580.

Primary Examiner—David T. Fox
Attorney, Agent, or Firm—Christie, Parker & Hale

[57] ABSTRACT

A process to assist in germination of spruce somatic embryos. The embryos are desiccated at humidity, preferably in the range of 85 to 99%. A process that differentiates somatic embryos of conifer comprises contacting embryogenic calli with a medium containing abscisic acid. A process for determining the quality of a plant to embryo is also described. That process comprises identifying the storage protein content of the embryo and comparing that content with the storage protein content of mature embryos of the same species.

5 Claims, 2 Drawing Sheets

PROCESS FOR THE PRODUCTION, DESICCATION AND GERMINATION OF CONIFER SOMATIC EMBRYOS

FIELD OF THE INVENTION

This invention relates to a process for the production, identification and germination of conifer somatic embryos.

DESCRIPTION OF THE PRIOR ART

The clonal propagation of trees, or indeed of any plant, offers a mechanism to derive the maximum possible advantage from genetic gains achieved in breeding programs (Hasnain and Cheliak, 1986). Recent advances in somatic embryogenesis of conifers have demonstrated that embryogenesis of this type provides a potential of sustained propagation of the conifers (Hakman and von Arnold, 1988; Gupta and Durzan, 1987). However, published results for the differentiation of somatic embryos show low germination rates and poor performance of the resulting plants (Durzan and Gupta, 1987; Boulay et al, 1988). This appears at least in part to be due to precocious germination of the embryo in vitro. This can have an adverse effect on seed germination (Bewley and Black) Bewley, J. D. and Black, M. (1985) "Maturation Drying, the Effects of Water Loss on Development in Seeds"; Physiology of Plant Development, Chapter 2.4; Plenum Press N. Y. P. 70-73.

It is important to improve the differentiation process to produce somatic embryos of higher quality. Redenbaugh et al. (1986) recognized the relationship between the degree of maturation achieved during somatic embryogenesis and quality of the resulting plantlets. These authors have proposed that the presence of storage proteins may be a good marker to assess embryo quality. Storage proteins begin to accumulate during the latter stages of embryo maturation and would identify somatic embryos that have completed this phase of embryogenesis. Plantlets produced from somatic embryos of alfalfa and cotton that contained higher levels of storage proteins were more vigorous compared to somatic embryos with lower levels of these proteins (Redenbaugh et al. 1986; Shoemaker et al. 1987). Considering that storage proteins are generally absent or present at low levels in somatic embryos when compared to their zygotic counterparts, poor vigour may well be attributed to poor maturation of somatic embryos (Crouch, 1982).

Several lines of evidence suggest that abscisic acid (ABA) may have an important role in embryogenesis. The ABA content of maize kernels reaches a peak during the initial periods grain filling (Jones and Brenner, 1987) while a biphasic change is observed in developing embryos of Arabadopsis (Karssen et al. 1983). Somatic embryos of carrot contain low levels of ABA during early development, the levels reach a peak and then decline during maturation (Kamada and Harada, 1982). These changes indicate that ABA may have a role during early to late stages of maturation. Exogenous application of ABA to immature zygotic embryos suggests that ABA specifically inhibits precocious germination, promotes maturation and the accumulation of storage proteins (Finklestein et al., 1985; Ackerson, 1984; Kuhlemeir et al., 1987). Recently, Michler and Lineberger (1987) found the light treatments that promote maturation (the formation of cotyledons) also increased levels of endogenous ABA in carrot somatic embryos. In addition, ABA suppresses the formation of aberrant embryo structures during somatic embryogenesis (Ammirato, 1974; Kamada and Harada, 1982).

Somatic embryogenesis has now been achieved for several conifer species and ABA has identified as an important media component for differentiation of somatic embryos of Norway spruce (Hakman et al., 1985; Hakman and von Arnold, 1988; Gupta and Durzan, 1987; Dunstan, 1988). Although these authors have shown that ABA promotes the differentiation of somatic embryos, little information was provided on the effects of ABA on maturation or embryo quality (Becwar et al., 1987; von Arnold and Hakman, 1988, Boulay et al. 1988).

In nature desiccation is a feature of embryo development and it is being suggested that desiccation has a role in the transition from maturation to germination. It is well documented that for many species desiccation enhances seed germination. For example, zygotic embryos of Ricinus communis require desiccation to achieve a high frequency of germination and normal radical elongation. The ability to arrest the development of somatic embryos may also be important in handling of somatic embryos during dissemination.

RELEVANT LITERATURE:

The relevant literature on desiccation includes Hasnain et al., 1986, Tissue Culture in Forestry:Economic and Genetic Potential, The Forestry Chronicle (August): 219215 which discusses clonal propagation of conifers.

Becwar, M. R., S. R. Wann, M. A. Johnson, S. A. Verhagen, R. P. Feirer and R. Nagmani, 1988. Development and characterization of in vitro embryogenic systems in conifers. In: M. R. Ahuja [Ed.], Somatic cell genetics of woody plants, Kluwer Academic Publishers, Dordrecht, The Netherlands, pp. 1-18.

Boulay, M. P., P. K. Gupta, P. Krogstrup, and D. J. Durzan, 1988. Development of somatic embryos from cell suspension cultures of Norway spruce (Pices abies Karst). Plant Cell Reports (7): 134-137.

Carman, J. G. (1988) Improved somatic embryogenesis in wheat by partial simulation of the in-ovulo oxygen, growth-regulator and desiccation environments. Plants (175): 417-424.

Durzan, D. J. and P. K. Gupta, 1987. Somatic embryogenesis and polyembryogenesis in Duoglas-fir cell suspension cultures. Plant Science (52): 229-235.

Gray, D. J., B. V. Conger, and D. D. Songstad, (1987) Desiccated quiescent somatic embryos of orchard grass for use as synthetic seeds. In Vitro Cellular and Developmental Biology. 23:29-33.

Gupta, P. K. and D. J. Durzan, 1987. Biotechnology of somatic polyembryogenesis and plantlet regeneration in lobiolly pine. Bio/tech. 5:147-151.

Hakman, I. and S. von Arnold, 1988. Somatic embryogenesis and plant regeneration from suspension cultures of Pices glauca (white spruce). Physiol. Plant. 72:579-587.

Hasnain, S. and W. Cheliak, 1986. Tissue Culture in Forestry.: Economic and Genetic Potential. The Forestry Chronicle (August): 219-225.

Kermode A. R., and J. D. Bewley, (1985) the role of drying in the transition from seed development to germination. J. Exp. Bot. 36:1906-1915.

Owens, J. N. and M. Molder, 1984. The reproductive cycle of interior spruce. Published by Information Services Branch British Columbia Ministry of Forests, Victoria, B. C. V3W 3E7.

Parrott, W. A., G. Dryden, S. Vogt, D. F. Hilderbrand, G. B. Collins, E. G. Williams, (1988) Optimization of somatic embryogenesis and embryo germination in soybean. In Vitro Cellular and Developmental Biology. 24:817-820.

Redenbaugh, K., J. Fujii, D. Slade, P. Visa, and M. Kossler (1986) Synthetic seeds-encapsulated somatic embryos. In Agronomy: Adjusting to a Global Economy. American Society of Agronomy Crop, Science Society of America, Soil Science Society of America; 78th Annual Meeting Program.

Redenbaugh, K., B. D. Paasch, J. W. Nichol, M. E. Kossler, P. R. Viss, and K. Walker (1986) Somatic seeds: Encapsulation of asexual plant embryos. Bio/-Technology 4:797-781.

As to maturation the relevant literature includes:
Ackerson, R. C. (1984). Regulation of soybean embryogenesis by abscisic acid. Jour. of Exp. Bot. 35, 403-413.

Ammirato, P. V. (1974). The effects of abscisic acid on the development of somatic embryos from cells of caraway (Carum carvi L.). Bot. Gaz. 135, 328-337.

Barratt, D. H. P. (1986). Modulation by abscisic acid of storage protein accumulation in Vicia faba L. cotyledons cultured in vitro. Plant Sci. 46, 159-167.

Becwar, M. R., Noland, T. L. and Wann, S. R. (1987). A method for quantification of the level of somatic embryogenesis among Norway spruce callus lines. Plant Cell Rep. 6, 35-38.

Boulay, M. P., Gupta, P. K., Krogstrup, P. and Durzan, D. J. (1988). Development of somatic embryos from cell suspension cultures of Norway spruce (Picea abies Karst.). Plant Cell Rep. 7, 134-137.

Carman, J. G. (1988). Improved somatic embryogenesis in wheat by partial simulation of the in-ovulo oxygen, growth-regulator and desiccation environments. Plants 175, 417-424.

Crouch, M. L. (1982). Non-zygotic embryos of Brassica napus L. contain embryo-specific storage proteins. plants 156, 520-524.

Dunstan, D. I. (1988). Prospects and progress in conifer biotechnology. Can. J. For. Res. 18, 1497-1506.

Durzan, D. J. and Gupta, P. K. (1987). Somatic embryogenesis and polyembryogenesis in Douglas-fir cell suspension cultures. Plant Sci. 52, 229-235.

Jones, R. J. and Brenner, M. L. (1987). Distribution of abscisic acid in maize kernel during grain filling. Plant Physiol. 83, 905-909.

Finkelstein, R. R., Tenbarge, K. M., Shumway, J. E., and Crouch, M. L. (1985). Role of ABA in maturation of rapeseed embryos. Plant Physiol. 78, 630-636.

Flinn, B. S., Roberts, D. R., Webb, D. T. and Sutton, B. C. S. Storage protein changes during zygotic embryogenesis in interior spruce. (Submitted to Plant Physiol.).

Ghosh, S., Gepstein, S., Heikkila and Dumbroff, EB. (1988). Use of a scanning densitometer or an ELISA plate reader for measurement of nanogram amounts of protein in crude extracts from biological tissues. Anal. Biochem. 169, 227-233.

Hakman, I. and von Arnold, S. (1985). Plantlet regeneration through somatic embryogenesis in Picea abies (Norway Spruce). J. Plant Physiol. 121, 149-158.

Hakman, I., and von Arnold, S. (1988). Somatic embryogenesis and plant regeneration from suspension cultures of Picea glauca (White spruce). Physiol. Plant. 72, 579-587.

Karssen, C. M., Brinkhorst-van der Swan, D. L. C., Breekland, A. E. and Koornneef, M. (1983). Induction of dormancy during seed development by endogenous abscisic acid: studies on abscisic acid deficient genotypes of Arabidopsis thaliana (L.) Heynh. Planta 157, 158-165.

Kuhlemeier, C., Green, PJ, and Chua, N. (1987). Regulation of gene expression in higher plants. Ann. Rev. Plant Physiol. 38, 221-57.

Kamada, H. and Harada, H. (1981). Changes in the endogenous level and effects of abscisic acid during somatic embryogenesis of Daucus carota L.

Laemmli, U. K. (1970). Cleavage of structural proteins during the assembly of the head of the bacteriophage T. Nature 227, 680-685.

Michler, C. H., and Lineberger, R. D. (1987). Effects of light on somatic embryo development and abscisic acid levels in carrot suspension cultures. Plant Cell, Tissue and Organ Culture 11, 189-207.

Redenbaugh, K., Paasch, B. D., Nichol, J. W., Kossler, M. E., Viss, P. R. and Walker, K. A. (1986). Somatic Seeds: Encapsulation of asexual plant embryos. Bio/tech. 4, 797-781.

Shoemaker, R. C., Christofferson, S. E. and Galbraith, D. W. (1987). Storage protein accumulation patterns in somatic embryos of cotton (Gossypium hirsutum L.). Plant Cell Rep. 6, 12-15.

Stuart, D. A., Nelsen, J. and Nichol, J. W. (1988). Expression of 7S and 11S alfalfa seed storage proteins in somatic embryos. J. Plant Physiol. 132, 134-139.

von Arnold, S., and Hakman, I. (1988). Regulation of somatic embryo development in Picea abies by abscisic acid (ABA). J. Plant Physiol. 132, 164-169.

Walton, D. C. (1980). Biochemistry and physiology of abscisic acid. Ann. Rev. Plant Physiol. 31, 453-489.

SUMMARY OF THE INVENTION

The present invention provides means of greatly increasing germination of conifer somatic embryo and assisting greatly in synchronizing germination and vigourous root elongation.

Accordingly, in a first aspect, the present invention is a process for the production of mature somatic embryos of conifers that comprises desiccating the embryo at humidities of less than 99.9%.

Preferably the conifer is spruce.

Preferably the humidity is in the range 85 to 99%.

In a second aspect the present invention is a process to differentiate somatic embryos of conifer that comprises contacting embryogenic calli with a medium containing abscisic acid (ABA).

The abicisic acid may be present in the amount 30 $\mu$M to 40 $\mu$M.

Preferably the medium includes indole butyric acid (IBA).

EXPERIMENTAL SECTION

Of the drawings referred to in this section:

TISSUE CULTURE

Figure 1:
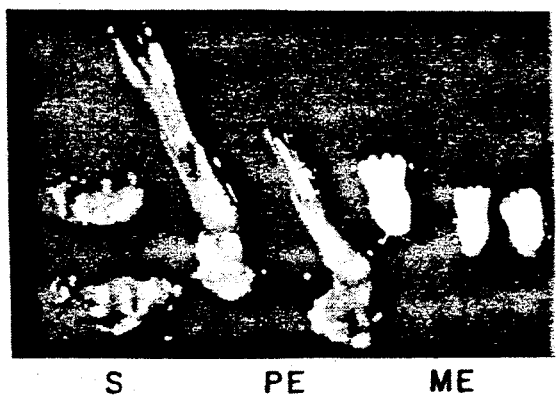
FIG. 1 shows the effect of abscisic acid on the morphology of finished embryo types.

Embryogenic calli were initiated from immature embryos of interior spruce (*Picea glauca/Picea engelmannii*) as described previously by Webb et al. (1989). Calli were maintained in the dark on VE basal media (amino acids added after autoclaving) containing 5 μM 2,4-D, 2 μM BA, 1% sucrose (proliferation media) at 27° C. and subcultured biweekly. Prior to further hormone treatments, calli (each weighing approximately 100 mg) were transferred from proliferation media to VE basal media containing 1% activated charcoal and 3.4% sucrose for one week in the light (16 hr photoperiod at 25-35 μeinsteins $M^{-2} sec^{-1}$). Further differentiation of somatic embryos was carried out in the light on VE basal media containing 3.4% sucrose and various levels of ABA and/or IBA with biweekly subculturing. Differentiated structures were removed from the calli, screened, weighted and stored at −70° C. for protein analysis. For germination studies, individual structures were removed from the calli and placed in 8 dram shell vials (7 per vial) containing 10 mls of ¼ VE basal media and 3.4% sucrose solidified in a slant with 0.54% Noble Agar. Counting of embryo types and morphological characterizations were carried out using a dissecting microscope.

PROTEIN ANALYSIS

Samples were removed from −70° C. storage and kept at 4° C. during the protein extraction. Solubilizing buffer (0.125M Tris-HCl pH 6.8 containing 22.5% mercaptoethanol, 9% SDS and 22.5% glycerol) was added to embryo samples (30 μl/mg tissue), homogenized in a microfuge tube using a power driven pestle and centrifuged for 10 min at 16,000×g. Sample protein was determined by a modified procedure of Ghosh et al. (1988). The disclosure of which is incorporated herein by reference. Sample (2 μl) was pipetted onto Whatman #1 filter paper, allowed to dry and stained with coomassie blue. The filter to air dry. The sample spots were cut out and the stain was eluted in 1 ml of 1% SDS and protein level was determined by absorbance at 590 and comparison to protein (BSA) standards. Samples (15 μg protein/lane) were fractionated by SDS-PAGE on 12% polyacrylamide gels with a 5% stacking gel (Laemmli, 1970). Following fixation gels were stained with coomassie blue.

PREGERMINATION

Pregermination treatments included placing mature embryos in Petri plates on water-saturated kimpaks (WSK), on petri plates at room humidity (AD), or in 6 wells of a 12 well Petri plate with the other six wells filled ⅔ full with sterile water (ADM). These treatments were carried out at 27° C. In order to identify the optimum humidity for desiccation, the embryos were incubated in an enclosed air space (24 cm diameter desiccator) exposed to a saturated salt solution. To achieve humidities of 95%, 90%, 81%, and 75%; atmospheres were exposed to saturated solutions of sodium phosphate-dibasic, zinc sulfate, ammonium sulfate, and sodium chlorate, respectively (Merck Index).

Embryos were transferred to soil following approximately 4 weeks on the germination media. Plantlets from ADM treated and non-treated controls (only embryos with roots were used) were placed on sterile peat pellets saturated with ¼ VE basal medium (no sucrose) inside a sterile GA7 magenta vessel. The plantlets remained in the closed vessel under 16 h photoperiod at a light intensity of 50 μE/m/sec (incandescent and grow lux lights) for 2 weeks. At this time the Magenta lid was removed and replaced with polyvinylidene chloride film and the vessel humidity was gradually reduced over 2 weeks by increasing the number of holes in the cover. Plants that were rated as survivors were over 2 cm in height and growing vigorously.

RESULTS

Maturation/Differentiation

Embryogenic calli of interior spruce proliferate, but do not differentiate beyond the proembryo stage on media containing 2,4 dichlorophenoxy acetic acid (2,4-D) and benzyladenine (BA). Little or no differentiation occurs when embryogenic calli are transferred to media without ABA (Table 1). Under these conditions the callus browns and becomes necrotic and in some cases a few structures can develop. When media levels of ABA are increased to 1-10 μM "shooty" structures predominate in many callus lines (FIG. 1). These shoots are aberrant and differ from embryos by the presence of a basal callus, elongated (shooty) cotyledons and poor hypocotyl development. The formation of shooty structures is inhibited at higher levels of ABA and bipolar embryos develop (Table 1). These embryos have well organized cotyledons, an elongated hypocotyl and are bipolar in that they have an obvious root apex on the basal end.

Figure 5:
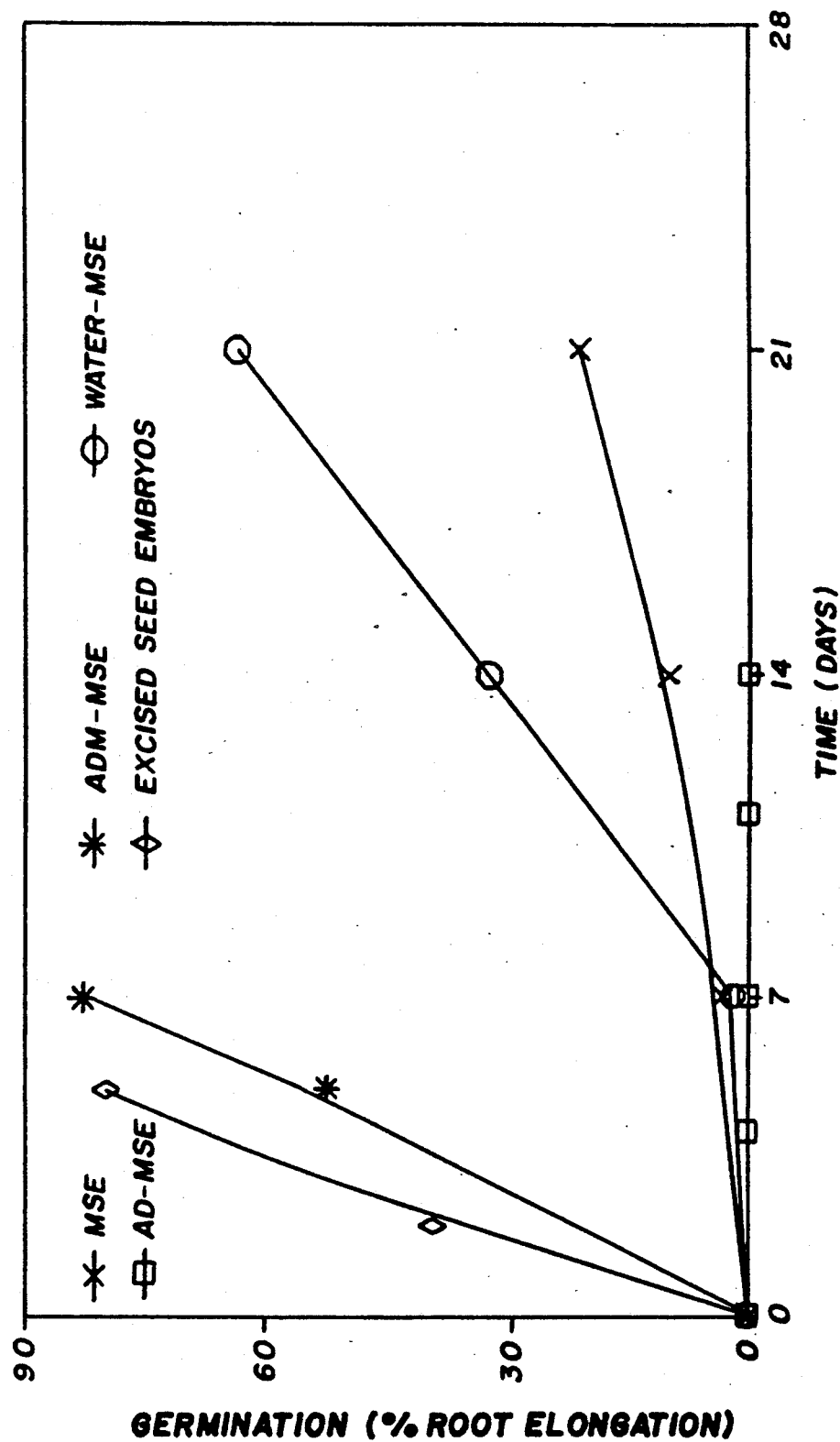
FIG. 5 compares the rates of germination for different maturation treatments.

The course of embryo maturation is also dramatically affected by ABA. Somatic embryos differentiated on 10-20 μM ABA germinate precociously but as the levels of ABA are increased, premature germination is inhibited, opaque cotyledonary structures characteristic of mature zygotic embryos are formed (FIG. 1 and Table 1). FIG. 5 relates germination, measured as percentage of root elongation to time for various maturation treatments. Table 1 shows that shooty structures (S) predominated low levels of ABA (1 to 10 μM), precocious embryos (PE) that are formed on 10-20 μM ABA and mature embryos (ME) produced on levels of ABA about 30 μM. Once the mature embryos are formed they appear to enter a stage of quiescence since they do not develop further on this medium, but germinate readily when transferred to medium without hormones. The optimal levels of ABA for the production of mature embryos for line 11 was 40 μM. There was considerable variation in the sensitivity of different lines to ABA. For instance, the majority of somatic embryos from line 8977 germinate precociously up to 50 μM ABA (Table 1). Our results support earlier observations where ABA promoted the differentiation of conifer embryogenic callus (von Arnold and Hakman, 1988; Boulay et al., 1988). However, it is not clear whether levels of ABA used in these studies were sufficient to prevent precocious germination. The ability of ABA to inhibit precocious germination of zygotic embryos is well documented (Finklestein and Crouch, 1985; Walton; 1980).

TABLE 1
ABA Effects on Differentiation of Somatic Embryos

| ABA | Clone 11 Number per Callus | | | Clone 8977 Number per Callus | | |
|---|---|---|---|---|---|---|
| μ | S | PE | ME | S | PE | ME |
| 0 | 10 ± 4[b] | 0 | 0 | 0 | 0 | 0 |
| 1 | 20 ± 6 | 3 ± 1 | 0 | 0 | 0 | 0 |
| 10 | 36 ± 9 | 17 ± 5 | 5 ± 2 | <1 | 36 ± 6 | <1 |
| 20 | 17 ± 6 | 5 ± 3 | 10 ± 5 | <1 | 59 ± 9 | 4 ± 2 |
| 30 | 2 ± 1 | <1 | 17 ± 4 | 1 ± 1 | 92 ± 18 | 2 ± 1 |
| 40 | 1 ± 1 | <1 | 37 ± 6 | 0 | 47 ± 12 | 25 ± 4 |
| 50 | 1 ± 1 | 0 | 25 ± 7 | 0 | 44 ± 13 | 32 ± 6 |

[a]S = shoots; PE = precocious embryos; ME = mature embryos.
[b]Mean ± SE for 9 calli per treatment.

Figure 2:
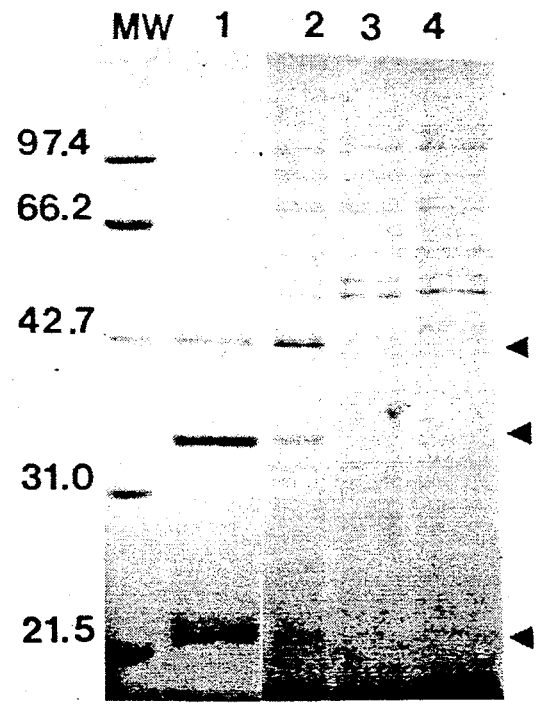
FIG. 2 is SDS-PAGE analysis of finished embryo types.
Figure 3:
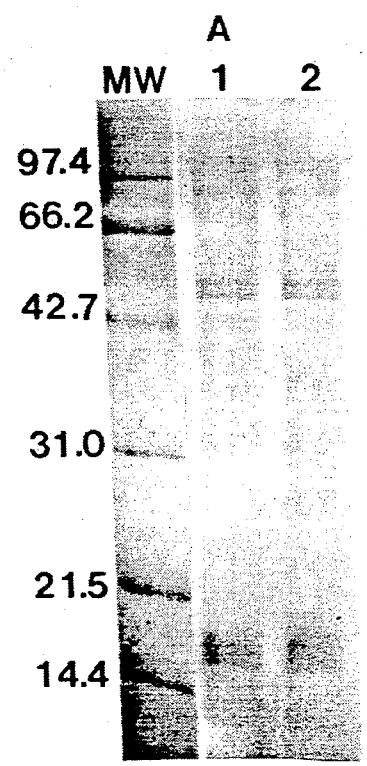
FIG. 3 shows protein profiles of precocious embryos differentiated with relatively low quantities of ABA.
Figure 4:
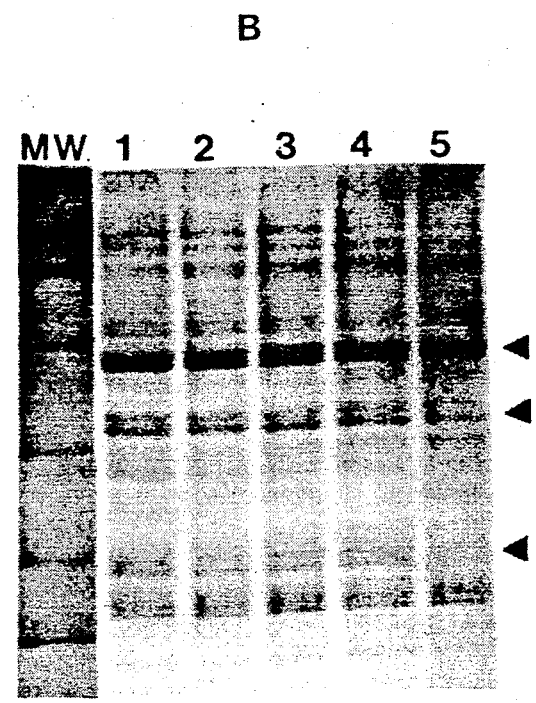
FIG. 4 shows protein profiles of mature embryos differentiated with relatively large quantities of ABA.

A comparison of the different embryo types (i.e. "shoots", precocious germinants and mature embryos) by SDS-PAGE reveals that only mature embryos accumulate proteins of 41, 33, 24 and 22 kD (FIG. 2). In FIG. 2 total protein (15 μg/lane) was run in lanes 1 to 4 along with molecular weight standards (MW). Protein was extracted from isolated protein bodies of mature seed embryos of interior spruce (lane 1), mature embryos (lane 2), precocious embryos (lane 3) and shoots (lane 4). Samples were separated on a 12% gel, fixed and then stained with coomassie blue. The migration distance of the prominent storage proteins is indicated by the arrows. These proteins correspond to the storage proteins found in protein bodies isolated from mature seed embryos of interior spruce (FIG. 2; Flinn et al., unpublished results). Precocious germinants formed on the same levels of ABA that stimulate the accumulation of storage proteins in mature embryos do not contain detectable levels of storage proteins —FIGS. 2 and 4. FIG. 3 shows protein profiles of precocious embryos that were differentiated on 10 μM ABA (lane 1) and 20 μM ABA (lane 2) and molecular weight markers and FIG. 4 shows protein profiles of mature embryos that were differentiated on 50 μM ABA (lane 1), 40 μM ABA (lane 2), 30 μM ABA (lane 3), 20 μM ABA (lane 4), 10 μM ABA (lane 5) and molecular weight markers (MW). The migration distance of the prominent storage proteins is indicated by the arrows. Hence, the accumulation of storage proteins appears to be a result of ABA inhibiting precocious germination and extending the period of maturation, rather than the absolute levels of ABA. These biomarkers are utilized to define the proper maturation protocol for somatic embryos. Although mature embryos were formed on media containing as little as 10 μM ABA, they contained lower levels of storage proteins than mature embryos produced on higher levels of ABA (FIGS. 3 and 4). Thus ABA appears to be regulating maturation and, as well, the degree to which storage proteins accumulate.

The present results suggest that including ABA in these cultures increases storage protein accumulation. Hakman and von Arnold (1988) report that somatic embryos of white spruce differentiated in the presence of ABA contain lipid and protein bodies.

Becwar et al. 1987 reported that equimolar concentrations of ABA and indole-3-butyric acid (IBA) promoted the differentiation of Norway spruce embryogenic callus. However, including IBA was detrimental to differentiation of Norway spruce when compared with the effects of ABA alone (von Arnold and Hakman, 1988). The present invention shows the effects of IBA on maturation of somatic embryos. Including low levels (0.1-10 μM) of IBA in the differentiation media enhanced the production of mature embryos (Table 2).

TABLE 2
IBA Effects on Production of Mature Embryos

| ABA/IBA (μM) | % OF CONTROL |
|---|---|
| 40/0 | 100 ± 12[a] |
| 40/0.1 | 135 ± 11 |
| 40/1 | 134 ± 12 |
| 40/10 | 138 ± 17 |
| 40/20 | 114 ± 18 |
| 40/40 | 59 ± 5 |

[a]Mean ± SE for 9 calli per treatment

In addition, cotyledonary development and general embryo morphology was improved under these conditions. However, at higher levels of IBA the embryos developed an enlarged hypocotyl. Carman (1988) found that a combination of auxin and ABA improved development of wheat somatic embryos. There was no effect of IBA on the accumulation of storage proteins in mature embryos or on their capacity for root elongation.

Redenbaugh et al. (1984) recognized a relationship between degree of maturation of somatic embryos and the vigour of the resulting plantlets. Plantlets derived from somatic embryos that contained higher levels of storage proteins were more vigorous and it was proposed that storage proteins could be used as a marker of embryo quality. The present invention shows that the course of embryo maturation has an effect on the subsequent quality of the plantlet. The conversion of somatic embryos of spruce is limited by the ability to obtain root elongation (Boulay et al., 1988; von Arnold and Hakman, 1988). Therefore frequency of root elongation was used as a criteria to evaluate embryo quality. Root elongation was routinely higher from mature embryos compared to precocious germinants and no root elongation was observed in shoots (Table 3).

TABLE 3

| ABA (μM) | ROOT ELONGATION % | | |
|---|---|---|---|
|  | S | PE | ME |
| 10 | 0 | 15 ± 8[b] | 28 ± 4 |
| 20 | 0 | 7 ± 7 | 21 ± 4 |
| 30 | 0 | — | 30 ± 13 |
| 40 | 0 | — | 26 ± 9 |
| 50 | 0 | — | 12 ± 7 |

[a]S = shoots; PE = precocious embryos; ME = mature embryos
[b]Mean ± SE for 60 structures per treatment It is clear that as embryo maturation was improved, embryo quality was also improved. However, the frequency of rooting within mature embryos was not directly associated with different levels of storage proteins. The increased accumulation of storage proteins in embryos of line 11 associated with differentiation on higher levels of ABA was not correlated with differences in their ability to root. Storage proteins can be used to identify the mature embryos and therefore represent biomarkers for determining embryo quality.

EFFECTS OF PREGERMINATION TREATMENTS ON EMBRYO GERMINATION

To assess the effects of desiccation on germination, mature somatic embryos were removed from maturation medium and either germinated directly on hormone free medium or pretreated for two weeks prior to germination. The pretreatments were air drying at ambient humidity (AD) drying at high humidity (ADM) or a water treatment (laying the embryos on a water-saturated Kimpac (WSK). Germination of mature embryos placed directly on germination medium was characterized by 2-3 weeks of hypocotyl/cotyledon elongation followed by a low frequency of root elongation Table 4. FIG. 5 shows that the percentage of embryos showing radical elongation was recorded at the specified times following placement on germination medium. Treatments carried out for 16 days include: Excised Seed Embryos; MSE, mature somatic embryos: Water-MSE, somatic embryos placed on water soaked Kimpaks; ADM-MSE, somatic embryos dried at high humidity; AD-MSE, somatic embryos dried at room humidity. The experiment has been repeated twice with similar results. Desiccation of embryos at ambient humidity (AD) resulted in 100% mortality. Pretreating the embryos on WSK lead to improved frequency of root elongation (about 70%) but shoot elongation still preceded that of the root by 2-3 weeks. Drying the embryos at high humidity (ADM) resulted in rapid germination which reached 80% after only 7 days. This latter treatment gave a germination frequency and rate comparable to that of zygotic embryos. Embryos incubated under ADM conditions for 16 days had lost an average of 10% fresh weight. This treatment has a similar effect on the rate and frequency of germination of embryos derived from other lines of embryogenic callus (Table 4). The humidity range that can be used for desiccation of somatic embryos without lethal effect is 85 to 99%.

These were exposed to the ADM treatment and germinated on a range of media. The germination medium was varied with respect to the concentration of the basal VE medium and the sucrose concentration. Embryos germinated on all media tested, however those differentiated in low levels (0-0.1 $\mu$M) of IBA give the highest germination frequencies (Table 2). The general trends of these results suggest that highest germination occurred on ½ strength VEHF with 2% sucrose with embryos differentiated in the presence of 0.1 $\mu$M IBA.

The effects of these treatments on root and shoot elongation was assessed two weeks after the embryos were placed on germination media. Little root elongation occurred on media containing 0.5 and 1% sucrose (<0.5 mm) and elongation data was not collected. Significant differences in the extent of elongation between maturation treatments and germination media were observed (Table 5). Low levels of IBA (0-1 $\mu$M) promoted root and shoot elongation. Embryos which were matured in the presence of higher levels of IBA performed better on higher (½ to full) media strengths. The best media for root elongation was ½ strength VEHF. Sucrose concentrations of 2 or 3.4% gave good shoot elongation but root elongation was greater at 3.4% sucrose. The combined effects of improved maturation treatments and germination media resulted in root elongation of over 2.5 cm in two weeks.

TABLE 5

The effects of germination medium on root and shoot elongation.

| | ¼ VE | | ½ VE | | 1 VE | |
|---|---|---|---|---|---|---|
| | 2% | 3.4% | 2% | 3.4% | 2% | 3.4% |
| ROOT ELONGATION (cm) | | | | | | |
| 40/0 | 0.70 ± .12 | 0.67 ± .36 | 0.72 ± .12 | 2.09 ± .18 | 1.08 ± .10 | 1.39 ± .20 |
| 40/.1 | 0.52 ± .13 | 1.82 ± .26 | 1.22 ± .18 | 2.62 ± .12 | 1.67 ± .22 | 1.54 ± .23 |
| 40/1 | 0.74 ± .3 | 1.87 ± .35 | 1.02 ± .24 | 2.0 ± .43 | 0.97 ± .02 | 1.17 ± .19 |
| 40/10 | <.5 | <.5 | 1.06 ± .13 | 1.87 ± .28 | 0.98 ± .15 | 0.98 ± .25 |
| 40/20 | <.5 | <.5 | <.5 | 2.03 ± .12 | 0.84 ± .14 | 0.98 ± .17 |
| 40/40 | <.5 | <.5 | <.5 | <.5 | <.5 | <.5 |
| NA | | | | | | |
| SHOOT ELONGATION (cm) | | | | | | |
| 40/0 | 0.30 ± .03 | 0.27 ± .04 | 0.39 ± .05 | 0.58 ± .06 | 0.65 ± .05 | 0.62 ± .06 |
| 40/.1 | 0.32 ± .05 | 0.38 ± .03 | 0.44 ± .04 | 0.35 ± .04 | 0.51 ± .05 | 0.53 ± .03 |
| 40/1 | 0.42 ± .04 | 0.27 ± .23 | 0.56 ± .07 | 0.55 ± .22 | 0.52 ± .04 | 0.40 ± .04 |
| 40/10 | <.3 | <.3 | 0.33 ± .04 | 0.33 ± .04 | 0.45 ± .06 | 0.57 ± .05 |
| 40/20 | <.3 | <.3 | <.3 | <.3 | 0.57 ± .07 | 0.47 ± .08 |
| 40/40 | <.3 | <.3 | <.3 | <.3 | <.3 | <.3 |

- Measurements made two weeks after germination initiated.

TABLE 4

The effects of desiccation on germination of different embryo genotypes.

| | | Root Elongation (%) | | |
|---|---|---|---|---|
| Genotype | Treatment | 7 days | 14 days | 21 days |
| 2 | Mature Embryos | 0 | 29 | 29 |
| | Desiccated | 91 | 91 | 91 |
| 5 | Mature Embryos | 0 | 0 | 3 |
| | Desiccated | 38 | 76 | 76 |
| 41 | Mature Embryos | 0 | 20 | 20 |
| | Desiccated | 82 | 90 | 90 |
| 44 | Mature Embryos | 0 | 24 | 24 |
| | Desiccated | 82 | 82 | 82 |

EFFECTS OF MODIFIED MATURATION AND GERMINATION MEDIA ON EMBRYO PERFORMANCE

Somatic embryos were differentiated on 40 $\mu$M ABA in combination with different concentrations of IBA.

Effect of ADM Treatment on Plantlet Survival Following Transfer to Soil

Plantlets derived from non-treated controls were found to set apical bud and enter an apparent state of dormancy soon after germination, whereas those from ADM embryos rarely showed this undesirable characteristic (Table 6). The desiccation treatment resulted in a general increase in vigour that was apparent in the relatively higher survival rate of these plantlets during conversion to soil and ambient humidity.

TABLE 6

The effects of desiccation at high humidity on transfer of plantlets to soil.

| Treatments | Survival (%) |
|---|---|
| Mature Embryos | 3.1 ± 3 |
| Desiccated Embryos | 47% |

During natural seed maturation, once the accumulation of storage reserves is completed, the seed begins to loose moisture and the embryo enters a period of desiccation (Owens and Moulder, 1984; Bewley and Black). Somatic embryos differentiated through the methods used in this work accumulate storage proteins and enter a period of quiescence. Simulating the latter stages of embryo development through desiccation at high humidity improves germination from 25 to 80%, causes synchronous germination and results in more vigourous root growth. These results are similar to those obtained from soybean somatic embryos (Parrott et al. 1988) where only sporadic germination could be achieved in the absence of a desiccation pretreatment and following desiccation germination was very genotype dependent. We have been able to obtain germination frequencies of 80-100% with the three genotypes. Furthermore, conversion to viable plants was obtained for all the germinants scored.

This is in contrast to orchard grass somatic embryos for which an overall conversation frequency of about 6% has been reported; much lower frequences have been reported for wheat somatic embryos following desiccation (Carman 1988).

It has been proposed that desiccation switches the genes expressed in the embryo from those required for maturation to those for germination. The present results are consistent with this hypothesis in that desiccation also promotes synchronized germination such that root elongation coincides with elongation of the hypocotyl/cotyledons. This pattern of germination more closely parallels that of zygotic embryos. Synchronized germination did not occur without a desiccation pretreatment of the embryos. Two features of early plantlet growth distinguished those derived from non-treated and desiccated embryos. Apical bud set was common in the non-treated plantlets, the conversion to soil (most likely an indication of plantlet vigour) was enhanced. Apparently, the biological clock that determines when the plant sets but is affected by the desiccation treatment.

In conclusion, the germination and early growth of spruce somatic embryos is enhanced by exposure to a desiccation treatment. Results obtained with spruce are comparable to those reported from alfalfa somatic embryos system which lends itself to an artificial seed system. Since the embryos produced are of high quality and withstand desiccation the prospects for an artificial seed system for spruce are promising. As to differentiation, ABA suppressed abnormal development, inhibited precocious germination and promoted maturation in somatic embryos of interior spruce. Mature embryos showed a greater capacity for root elongation, a critical process that limits their conversion into plantlets. Although, improved maturation had a beneficial effect on root elongation, the average frequency of 25% is still low and limits mass propagation of this species by somatic embryogenesis.

I claim:

1. A process for propagation of spruce somatic embryos which includes the steps of differentiating spruce somatic embryos in contact with a growth medium containing abscisic acid, separating the somatic embryos from said medium, and germinating the somatic embryos, characterized in that the embryos are matured on said medium and are partially dried prior to germination by exposing mature embryos separated from the said medium to an atmosphere having from greater than 85% up to 99% humidity.

2. The process of claim 1 wherein the humidity of the atmosphere is established in a closed area by the presence of liquid selected from the group consisting of:
   water; and
   an aqueous solution of a salt providing a humidity of from 90% to less than 99%, wherein the embryos are not in direct contact with said liquid while in the closed area.

3. The process of claim 2 wherein the liquid is an aqueous solution of a salt selected from the group consisting of:
   saturated sodium dihydrogen phosphate providing a humidity of about 95%; and
   saturated zinc sulphate providing a humidity of about 90%.

4. The process of claim 2 wherein the liquid is sterile water.

5. The process of claim 1 wherein the mature somatic embryos are derived from embryogenic calli initiated from immature embryos and wherein said somatic embryos are differentiated in contact with a growth medium containing 30-40 $\mu$M abscisic acid and 0.1-10 $\mu$M indole-3-butyric acid.

* * * * *